United States Patent [19] [11] Patent Number: 4,772,301
Bauer [45] Date of Patent: Sep. 20, 1988

[54] PROCESS FOR THE SEPARATION OF $C_{5+}$ HYDROCARBONS FROM A GASEOUS STREAM

[75] Inventor: Heinz Bauer, Munich, Fed. Rep. of Germany

[73] Assignee: Linde Aktiengesellschaft, Wiesbaden, Fed. Rep. of Germany

[21] Appl. No.: 62,744

[22] Filed: Jun. 16, 1987

Related U.S. Application Data

[63] Continuation-in-part of Ser. No. 943,024, Dec. 18, 1986, abandoned.

[30] Foreign Application Priority Data

Dec. 18, 1985 [DE] Fed. Rep. of Germany ....... 3544855

[51] Int. Cl.⁴ .............................................. F25J 3/02
[52] U.S. Cl. ........................................ 62/20; 62/27; 62/31; 62/39; 62/41
[58] Field of Search ...................... 62/9, 11, 16, 17, 20, 62/23, 24, 27–32, 34, 38–42; 55/29, 68

[56] References Cited

U.S. PATENT DOCUMENTS

| 3,882,689 | 5/1975 | Rogers | 62/9 X |
| 3,919,853 | 11/1975 | Rojey | 62/9 |
| 4,012,212 | 3/1977 | Kniel | 62/38 X |
| 4,272,269 | 6/1981 | Hammond et al. | 62/17 |
| 4,323,380 | 4/1982 | Muller et al. | 62/41 X |
| 4,428,759 | 1/1984 | Ryan et al. | 62/17 |
| 4,430,103 | 2/1984 | Gray et al. | 62/34 X |
| 4,435,198 | 3/1984 | Gray | 62/34 X |
| 4,507,133 | 3/1985 | Kahn et al. | 62/29 |
| 4,608,068 | 8/1986 | Bauer et al. | 62/31 X |
| 4,617,039 | 10/1986 | Buck | 62/28 X |

Primary Examiner—Steven E. Warner
Attorney, Agent, or Firm—Millen & White

[57] ABSTRACT

For the separation of $C_{5+}$ hydrocarbons from a gaseous stream containing light hydrocarbons, $C_1$–$C_5$, and, in some cases, lower boiling components, e.g., hydrogen, the gaseous feedstream, under pressure, is cooled, partially condensed, and separated into a liquid fraction and a gaseous fraction. The liquid fraction is separated by rectification under a lower pressure into a product stream consisting essentially of $C_{5+}$ hydrocarbons and a residual gas stream predominating in components lower boiling than $C_5$. The gaseous fraction separated after the partial condensation is introduced into a recontacting column wherein $C_{5+}$ components still contained in the gas are scrubbed out. The scrubbing step is performed with a partial condensate of the overhead product of the rectification. The loaded scrubbing liquid is then introduced into the rectification as reflux.

22 Claims, 2 Drawing Sheets

PROCESS FOR THE SEPARATION OF $C_{5+}$ HYDROCARBONS FROM A GASEOUS STREAM

CONTINUING DATA

This application is a Continuation-In-Part of copending U.S. application Ser. No. 943,024, filed Dec. 18, 1986 now abandoned.

This application is also related to copending U.S. applications Ser. No. 809,958, filed Dec. 17, 1985, now U.S. Pat. No. 4,707,171 and Ser. No. 809,953, also filed Dec. 17, 1985, now U.S. Pat. No. 4,705,549 both of which are herein incorporated by reference.

BACKGROUND OF THE INVENTION

This invention relates to a process for the separation of $C_{5+}$ hydrocarbons from a gaseous feedstream containing light hydrocarbons, e.g., natural gas or a refinery gas. Depending on the specific gas feedstream being treated, it may also contain components having a lower boiling point than methane, e.g., hydrogen. In particular, the invention relates to a process wherein the gaseous feedstream under elevated pressure is cooled, partially condensed and separated into a liquid fraction and a gaseous fraction, and the liquid fraction is separated by rectification into a product stream consisting essentially of $C_{5+}$ hydrocarbons and into a residual gas stream containing predominantly lower-boiling components.

In German Patent Application P No. 35 11 636.6, and U.S. application Ser. No. 809,958, a process is disclosed for the separation of $C_{2+}$ or of $C_{3+}$ hydrocarbons from a gaseous stream wherein, in one embodiment (see FIG. 2), prior to separation of these hydrocarbons, a fraction enriched in $C_{5+}$ hydrocarbons is obtained. This fraction enriched in $C_{5+}$ hydrocarbons is then introduced into a rectifying column wherein the $C_{2+}$ and, respectively, $C_{3+}$ hydrocarbons are also purified. Whereas the $C_{2+}$ and $C_{3+}$ product streams are withdrawn from the rectifying column via a side stream, the fraction containing the $C_{5+}$ hydrocarbons is withdrawn from the bottom of the column.

However, processes wherein the $C_2$ to $C_4$ or $C_3/C_4$ hydrocarbons mixture (LPG) are obtained as a side stream product from a column having an extensive separating range, are economically disadvantageous since even with a large number of plates in the rectifying column, high internal reflux ratios are required for the production of the side product in the pure form.

A high specific energy requirement is also created by the thermodynamic loss associated with the large temperature difference (for example, in the range of about 200° C.) required between the column head and the column bottom of a rectifying column providing $C_{2-}$ hydrocarbons as the overhead product and $C_{5+}$ hydrocarbons as the bottoms product. In addition, for the $C_4/C_5$ separation in the lower section of such a rectifying column, an unfavorably high pressure must be normally be employed for this specific separating function in order to provide satisfactory condensation conditions for the overhead product.

An alternative possibility of separating $C_{5+}$ hydrocarbons from such a gaseous mixture resides in first separating all of the $C_{2+}$ and, respectively, $C_{3+}$ hydrocarbons from such a gaseous mixture and then separating, from the thus-obtained product stream, in an additional debutanizer, the $C_{5+}$ hydrocarbons. This type of operation, though, is likewise unfavorable since an additional debutanizer is needed, entailing considerable additional investment and operating costs.

A simple preliminary separation of the $C_{5+}$ hydrocarbons by partial condensation is also usually unsatisfactory owing to the small relative volatility difference between butane and pentane. Therefore, for an adequate $C_{5+}$ separation, an undesirably large amount of $C_4$ is also condensed, which is especially disadvantageous in many instances since LPG (a $C_3/C_4$ mixture) frequently is in demand and would otherwise be producible in higher amounts.

SUMMARY OF THE INVENTION

An object of this invention is to provide an improved process of the type discussed hereinabove, especially a process enabling the separation of the $C_{5+}$ hydrocarbons from the gaseous stream without a large expenditure in investment and operating costs.

Another object is to provide a process capable of separating the $C_{5+}$ hydrocarbons as well as LPG in high yields from a gas containing $C_{5+}$ hydrocarbons, LPG, and lighter components.

Upon further study of the specification and appended claims, further objects and advantages of this invention will become apparent to those skilled in the art.

To attain these objectives in a process of the type discussed above, the liquid fraction separated after the partial condensation of the gaseous feedstream is expanded to a lower pressure prior to rectification, and the gaseous fraction separated after the partial condensation is introduced, definitely without any substantial reduction in pressure, into a recontacting column wherein residual $C_{5+}$ hydrocarbons in the gas are scrubbed out of the gaseous fraction. As the scrubbing agent, there is employed a condensate obtained during the rectification. The liquid fraction obtained in the bottom of the recontacting column is also expanded and then introduced into the rectification column.

Introduction of the gaseous fraction to the recontacting column without substantial reduction in pressure means that the pressure drop of the gaseous fraction between the separation and recontacting column is less than about 2.0 bar, preferably less than about 1.0 bar, and especially less than about 0.3 bar. This aspect of the invention permits to maintain the high feed gas pressure for the downstream process steps. Either the final gaseous product can be made available now under pressure or the pressure can be let down at a lower temperature level where the cooling effect is more valuable.

An underlying aspect of the process of this invention is that the $C_{5+}$ hydrocarbons are to be separated at a relatively high temperature and are not to be subcooled unnecessarily. In the recovery of the $C_{5+}$ hydrocarbons and the LPG from the lighter components, the separation is to be conducted in two discrete steps. Since adequate $C_{5+}$ separation cannot be attained by partial condensation alone, and since with additional production of LPG, a large portion of the $C_3$ hydrocarbons and, in particular, of the $C_4$ hydrocarbons would condense together with the $C_{5+}$ hydrocarbons, the invention provides that an additional self-cooled scrubbing step is performed in recontacting column wherein heavier components remaining in the gaseous phase after partial condensation are separated by contact with a lighter scrubbing liquid which is itself partially vaporized during the scrubbing step. In this process, a fraction free of $C_{5+}$ hydrocarbons, namely the overhead product obtained during the subsequent rectification of the condensate, is utilized as the scrubbing liquid. Rectification is oriented toward obtaining a $C_{5+}$ hydrocarbons fraction and thus can be performed under favorable conditions for separation of $C_4/C_5$ cut, especially under a relatively low pressure.

The liquid fraction withdrawn from the bottom of the recontacting column does contain the heavy components scrubbed out of the gaseous fraction, but the concentration of these components is substantially lower than that in the partially condensed liquid fraction of the feedgas. Therefore, in an advantageous further aspect of the invention, the liquid fraction obtained in the bottom of the recontacting column is introduced separately into the rectification, preferably as reflux liquid.

In the process of this invention, partial condensation for separating the $C_{5+}$ enriched fraction from the feedgas is usually conducted in a temperature range of about $+10°$ to $-15°$ C.

Rectification is advantageously performed so that the residual gas stream obtained at the head of the rectifying column no longer contains any $C_{5+}$ hydrocarbons whereas frequently a small proportion of $C_3$ and $C_4$ hydrocarbons can be permitted to be in the bottoms product. The rectifying conditions thus can be adjusted to minimize rectification costs while producing an adequate yield of an LPG fraction, irrespective of the small amounts of $C_3$ and $C_4$ hydrocarbons that are withdrawn in the bottoms product. Furthermore, a small residual content of $C_3$ and $C_4$ hydrocarbons in the $C_{5+}$ product stream of the rectification can in many instances be separated in the downstream facilities which are generally available. For example, a typical application for the process of this invention is in the processing of the refinery gas in a large complex where fractionating columns for $C_4/C_5$ separation are already on hand. Insofar as the $C_{5+}$ bottoms product from the rectification contains at this point relatively small amounts of the lighter components, such lighter components can frequently be removed in preexisting equipment at little additional expense.

The overhead product obtained during the rectification must be recompressed, prior to its use as scrubbing liquid in the recontacting column, to the elevated pressure of the gaseous stream to be fractionated. This is advantageously accomplished by partially condensing the residual gas of the rectification initially, for example, to an extent of 50-99%, preferably 70-95%, and by separating the thus-obtained liquid proportion and pumping same separately to a higher pressure, in order to be finally introduced into the recontacting column. The uncondensed proportion of the residual gas from the rectification can then be discharged as a residual gas stream at the lower pressure without compression. Partial condensation of the residual gas from the rectification can advantageously be conducted by cooling to temperatures of about $-25°$ to $-50°$ C.

The liquid fraction obtained during the partial condensation of the gaseous feedstream in an advantageous further development of the invention is heated, prior to rectification, at least partially against the gaseous feedstream to be cooled in order to set favorable rectification conditions.

If, besides the $C_{5+}$ fraction, another product of the process is to be an LPG fraction, then, in a further embodiment of the invention, the gaseous fraction exiting from the recontacting column is separated, by further cooling and partial condensation, into a further liquid fraction and gaseous fraction and the thus-obtained further liquid fraction is separated by an additional rectification into a further product stream containing essentially $C_{3+}$ hydrocarbons and into a further residual gas stream containing predominantly lower-boiling components. Instead of LPG production, the production of $C_2$ to $C_4$ fraction is desired, the procedure to be followed can be completely analogous.

In still another advantageous modification of this process, said further residual gas stream is at least partially engine-expanded to produce refrigeration. The pressure of the first rectification column for separation of the $C_{5+}$ hydrocarbons is then advantageously set so that it lies between the elevated pressure of the gaseous feedstream to be separated and the pressure of the engine-expanded further residual gas stream. The pressure in the first rectification column in this connection, is, in particular, advantageously set so close to the pressure of the further residual gas stream that the proportions that have not been condensed during condensation of the first residual gas can be introduced directly into the engine-expanded portion of the further residual gas. In this way, it is possible to obviate the need for separated discharge lines for two residual gas streams.

The process of the invention is particularly suitable for treating gas mixtures of the following general composition:

| | |
|---|---|
| $H_2$ | 10-90 mol % |
| $CH_4$ | 5-30 mol % |
| $C_2H_6$ | 3-25 mol % |
| $C_3H_8$ | 2-20 mol % |
| $C_4$ | 1-15 mol % |
| $C_{5+}$ | 0.2-10 mol %. |

A facility for conducting the process of this invention generally comprises at least one heat exchanger for the cooling and partial condensation of the gaseous stream, a phase separator for separating the partially condensed portion of the gaseous stream, a rectifying column for separation of the partially condensed portion of the gaseous stream, and a recontacting column, the lower zone of which is in communication with the vapor space of the separator and the upper zone of which is in communication with the head of the rectifying column. Another heat exchanger, a further phase separator, and pump are also incorporated between the head of the rectifying column and the upper zone of the recontacting column. In a preferred modification of the facility, the separator and the recontacting column are arranged in a container common to both of them, wherein the recontacting column is preferably located above the separator and is separated from the separator by a flue plate.

BRIEF DESCRIPTION OF THE DRAWINGS

Various other objects, features and attendant advantages of the present invention will be more fully appreciated as the same becomes better understood when considered in connection with the accompanying drawings, in which like reference characters designate the same of similar parts throughout the several views, and wherein.

Figure 1:
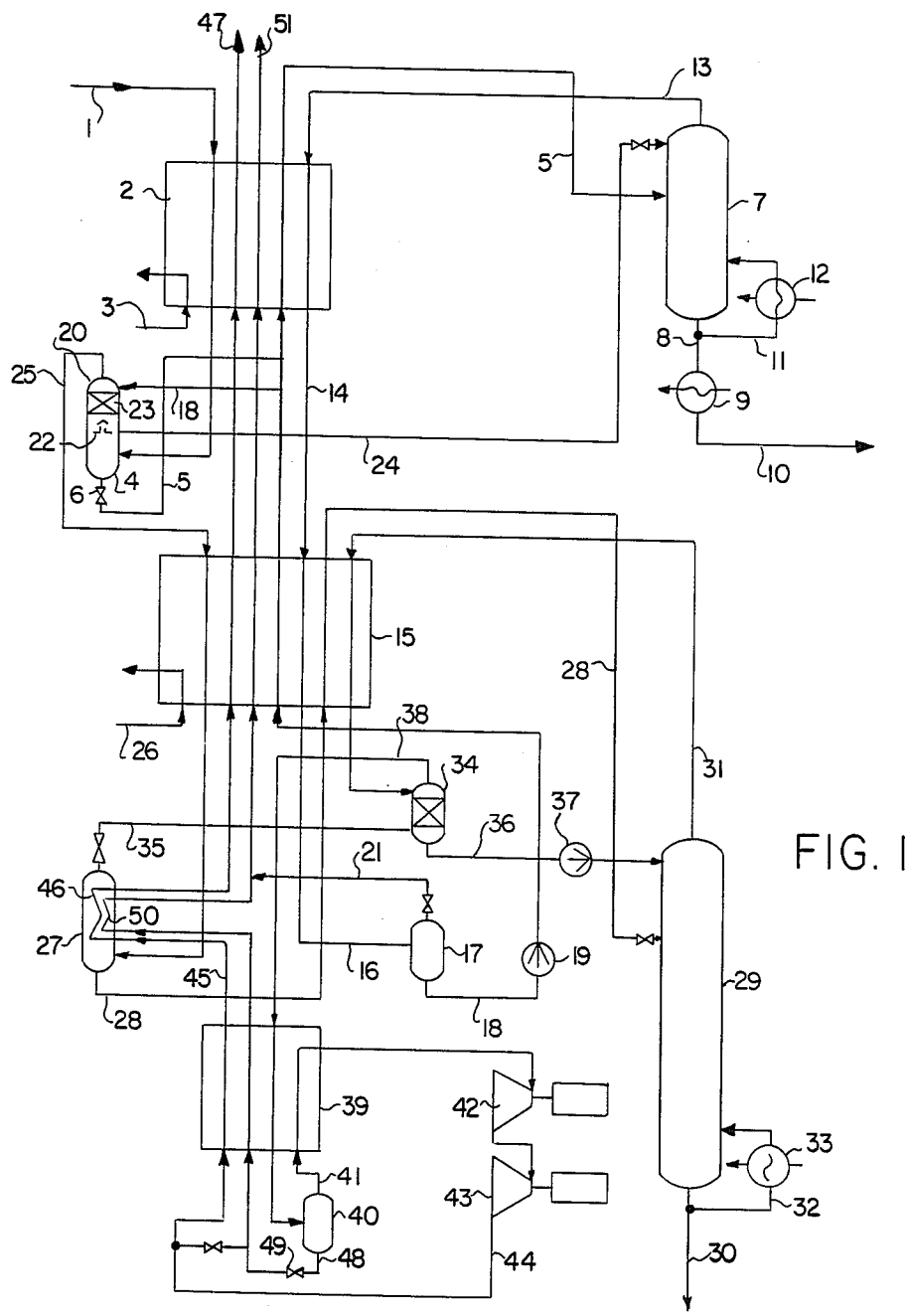
FIG. 1 is a schematic flowsheet of a preferred comprehensive embodiment of the invention.

In the installation shown schematically in FIG. 1, the gaseous mixture to be separated, e.g., a refinery gas or natural gas, is introduced via conduit 1 under elevated pressure, for example between 15 and 25 bar, and at approximately ambient temperature into a heat exchanger 2 wherein it is cooled against process streams to be heated as well as against a cooling cycle 3 to a sufficient extent to condense most of the $C_{5+}$ hydrocarbons as well as a portion of the $C_3$ and $C_4$ hydrocarbons in equilibrium therewith. In the separator 4, the thus-formed condensate separated from the gaseous fraction is withdrawn via conduit 5, expanded to a lower pressure in valve 6, and reheated in heat exchanger 2 before being introduced, after partial vaporization, in a rectifying column 7. Via conduit 8 a product stream is obtained in the bottom of the rectifying column 7 which consist essentially of $C_{5+}$ hydrocarbons as well as minor amounts of $C_3$ and $C_4$ hydrocarbons. This product stream is discharged, after being cooled in heat exchanger 9, via conduit 10 as the product and can be fed, for example, to a debutanizer that is generally present in a relatively large plant; in the debutanizer, the product stream can be further fractionated without much additional expenditure into $C_3/C_4$ fraction and a $C_{5+}$ fraction. A portion of the liquid withdrawn from the bottom of the rectifying column 7 is introduced via conduit 11 into a heat exchanger 12, heated therein, and recycled, as reboiler fluid into the lower zone of the rectifying column 7.

Rectifying column 7 generally operates at a pressure below the critical pressure of the liquid product stream, preferably at a pressure of 20–60% of the feed gas pressure. Typical operating pressures for column are about 5–15 bar. The operating temperatures of column 7 are generally about $-20°$ to $+50°$ C. at the head and about $+50°$ to $120°$ C. at the bottom. The temperature difference between the head and the bottom of column 7 is about 20–80K.

At the head of the rectifying column 7, via conduit 13, a light overhead product is obtained no longer containing any $C_{5+}$ hydrocarbons. This product is cooled in heat exchanger 2 and thereafter is passed via conduit 14 into a further heat exchanger 15 wherein most of the head product is condensed. The condensate is passed via conduit 16 into a phase separator 17 wherein the thus-formed liquid is separated and withdrawn via conduit 18. After increasing the pressure to the pressure of the crude gas by means of pump 19, the liquid is conducted through heat exchanger 15 and thereafter introduced to the head of a recontacting column 20. The residual gas stream obtained in separator 17 is withdrawn via conduit 21 and fed into a residual gas conduit which will be described below.

The recontacting column 20 is arranged above the separator 4 and separated from the latter by a flue plate 22. Through the flue plate, the gaseous fraction is passed from the separator 4 directly into the lower zone of the recontacting column where it is then passed upwardly through a mass transfer zone 23 containing packing or several plates, and into contact with the condensate fed via conduit 18. During this step, higher boiling components still present in the gas are scrubbed out whereas a portion of the scrubbing liquid is vaporized and remains in the gaseous fraction. In the lower zone of the recontacting column, a liquid is obtained loaded with higher boiling components; this liquid is withdrawn via conduit 24 and introduced as reflux liquid to the head of the rectifying column 7.

The gaseous fraction exiting from the recontacting column 20 is withdrawn via conduit 25 and is partially recondensed in heat exchanger 15 against process streams to be heated as well as against external refrigeration provided in a cooling cycle 26, in order to separate out $C_3$ and $C_4$ hydrocarbons. The thus cooled mixture is passed into a phase separator 27. Condensate is discharged therefrom via conduit 28, and after being reheated in heat exchanger 15 is passed into a further rectifying column 29 where it is separated into a bottoms LPG fraction discharged via conduit 30 and an overhead product containing lower-boiling components, said product being withdrawn via conduit 31. A portion of the bottoms LPG is branched off via conduit 32, heated in heat exchanger 33 and returned as reboiler fluid into the lower zone of column 29.

The overhead product withdrawn via conduit 31 from column 29 is cooled sufficiently in heat exchanger 15 to be partially condensed and is then introduced into a further recontacting column 34. The condensed proportion of the overhead product here scrubs the gaseous fraction withdrawn from the separator 27 via conduit 35. During this step, $C_3$ and $C_4$ hydrocarbons that have remained in this fraction are scrubbed out essentially at the pressure of rectifying column 29. The resultant liquid fraction is withdrawn via conduit 36 and conveyed by means of pump 37 as reflux liquid to the head of the rectifying column 29.

The gaseous fraction leaving the recontacting column 34 passes via conduit 38 into a further heat exchanger 39 and is cooled therein so that there are formed, by partial condensation and separation of the condensate in a separator 40, a gaseous fraction containing essentially hydrogen and a liquid fraction containing higher-boiling components. The hydrogen fraction is withdrawn via conduit 41, partially heated in heat exchanger 39, and then engine-expanded in two stages in expansion turbines 42, 43. The thus-expanded hydrogen is conducted via conduit 44 to the cold end of heat exchanger 39 and is heated in heat exchange against the gaseous stream introduced via conduit 38. Subsequently, the hydrogen is passed via conduit 45 into a heat exchanger 46 arranged within separator 27 and here cooling the gaseous fraction further, thereby to separate a portion of the $C_3$ and $C_4$ hydrocarbons that have remained in the gas. Thereafter, the hydrogen is further heated in heat exchangers 15 and 2, and is discharged from the installation as a product stream via conduit 47.

The liquid fraction obtained in separator 40 is withdrawn via conduit 48, expanded in valve 49, and thereafter heated in heat exchanger 39. Also this fraction is subsequently further heated in phase separator 27 against the gaseous fraction present therein; for this purpose, heat exchanger 50 is provided. Then, after being mixed with the residual gas conducted via conduit 21 from separator 17, the resultant mixture is heated in heat exchangers 15 and 2 and is finally discharged as a residual gas fraction via conduit 51. The compositions, flow rates, temperatures and pressures of many of the streams for the Example illustrated in FIG. 1 are provided in Tables I and II.

TABLE I

| components molar % | feed gas stream | (1) | (5) before heat exchange | (5) after heat exchange | (10) | (13) | (18) before heat exchange | (18) after heat exchange | (21) | (24) | (25) |
| --- | --- | --- | --- | --- | --- | --- | --- | --- | --- | --- | --- |
| $H_2$ | 48.4 | 48.4 | 1.7 | — | | 2.5 | 0.2 | | 30.7 | 1.8 | 50.6 |
| $C_{3-}$ | *46.0 | 46 | 58.2 | | 11.9 | 81.3 | 82.3 | | 68.6 | 62.5 | 47.4 |
| $C_4$ | 4.5 | 4.5 | 28.3 | | 63.1 | 15.7 | 16.9 | | 0.8 | 32.1 | 2 |
| $C_{5+}$ | 1.1 | 1.1 | 11.8 | | 25 | 0.5 | 0.5 | | <0.1 | 3.1 | <0.1 |
| other | <0.1 | <0.1 | <0.1 | | <0.1 | <0.1 | <0.1 | | <0.1 | 0.5 | <0.1 |
| flow/(kmol/hr) | 1148.4 | 1148.4 | 81 | | 47.5 | 109 | 100.9 | | 8.1 | 75.5 | 212 |
| temperature/°C. | 37 | 10 | 10 | 31 | 75 | 28 | −29 | 7 | −35 | 0 | −35 |
| pressure/bar | 32.2 | 32 | 32 | vapor 10 / liquid 10 | 10.2 | 10 | 35 | 34.7 | 9.4 | 10 | 31.5 |

*46% $C_{3-}$ = 18% $CH_4$ + 16% $C_2H_6$ + 12% $C_3H_8$

TABLE II

| components molar % | stream (30) | stream (47) | stream (51) |
| --- | --- | --- | --- |
| $H_2$ | — | 98.2 | 12.1 |
| $C_{3-}$ | 85.9 | 1.8 | 87.9 |
| $C_4$ | 14.0 | — | — |
| $C_{5+}$ | 0.1 | — | — |
| other | — | — | — |
| flow/(kmol/hr) | 154.2 | 512.4 | 434.3 |
| temperature/°C. | 84 | 33 | 33 |
| pressure/bar | 30.7 | 10 | 5.5 |

Figure 2:
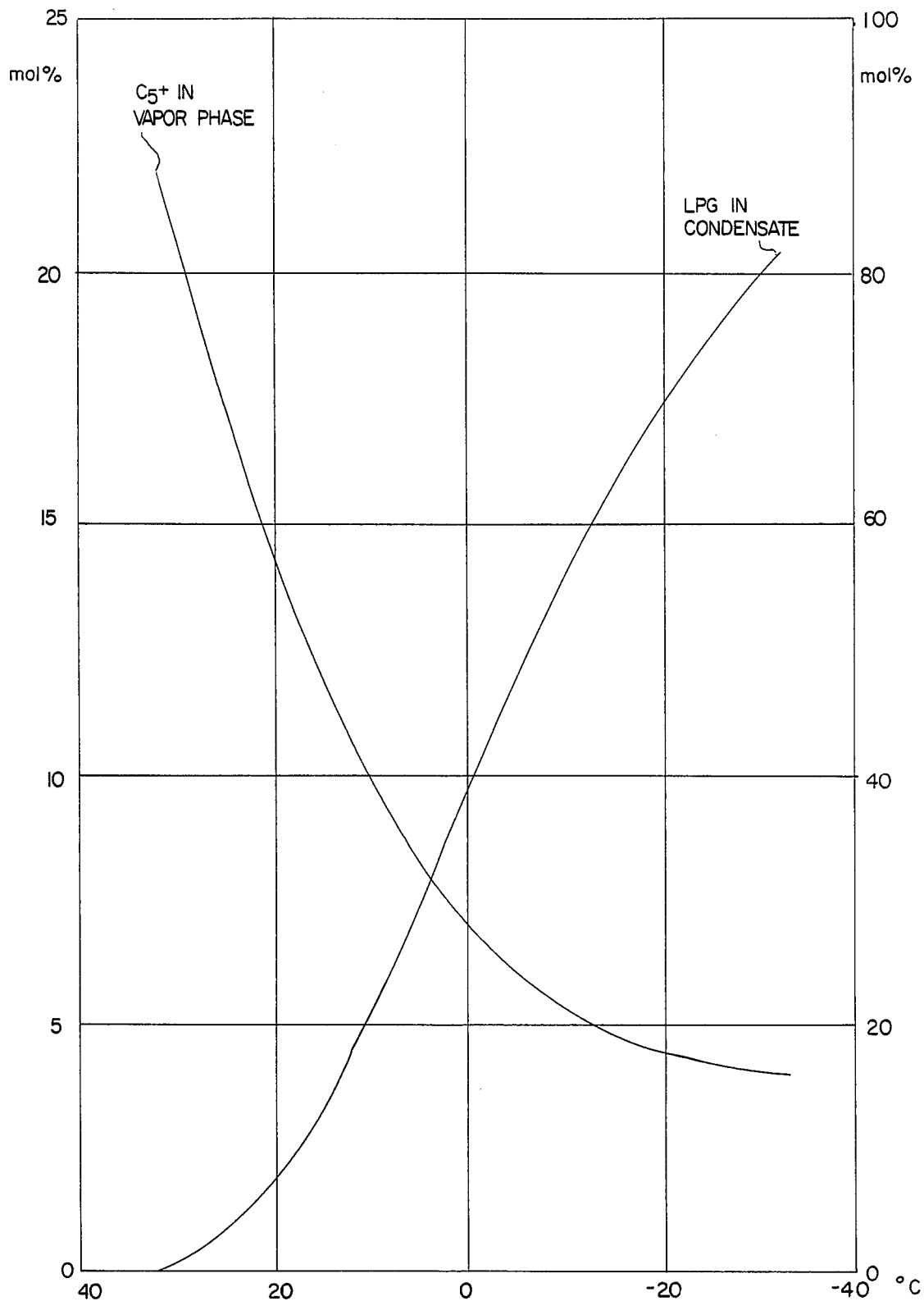
FIG. 2 is a graph illustrating the effect of the temperature on the quantity of the $C_{5+}$ hydrocarbons remaining in the vapor phase during condensation of the feed gas mixture, as well as the quantity of LPG in the condensate.

In FIG. 2, the compositions of the fractions obtained in separator 4 are plotted as a function of the temperature. In order to attain a sufficiently high separation of $C_{5+}$ hydrocarbons which will permit the elimination of a subsequent treatment of the LPG product obtained in column 29, it is generally necessary to provide that the gaseous fraction to be further fractionated, i.e., the non-condensed gas in separator 4, contain a residual content of $C_{5+}$ hydrocarbons of less than 3%, for example 2%. It can be seen from FIG. 2 that this can be accomplished by partial condensation only if the gas, prior to phase separation, is cooled to very low temperatures. However, this entails the disadvantageous effect that at that point a very large proportion of the $C_3/C_4$ components is concomitantly condensed as well. Consequently, only a relatively small amount of LPG product of adequate purity can be obtained from the rectifying column 29. For example, with a typical partial condensation temperature of +3° C., an unduly high $C_{5+}$ hydrocarbon content is obtained in the gaseous phase, being about 8 mol %. Furthermore, about 32 mol % of LPG is condensed in the liquid phase and lost for the subsequent separating stage. Due to the high LPG proportion of this fraction, further processing in conventional rectification columns frequently available in refineries is realizable only at a substantial expense. In comparison, with the use of the process of this invention, with the same gas mixture in conduit 25, the result is a gas composition with merely about 2.3 mol % of $C_{5+}$ hydrocarbons, while simultaneously the $C_{5+}$ fraction obtained in conduit 10 contains about 22% of the LPG present in crude gas so that about 78% of the LPG present in the crude gas can be discharged via conduit 30 as a product stream having the desired purity. The figures given above are valid for a slightly changed feed gas composition. For the feed gas listed in Table I, stream (1) the $C_{5+}$ fraction obtained in conduit 10 would contain even less LPG. In this case stream 10 contains 18.7% of the LPG present in the crude gas.

The preceding example can be repeated with similar success by substituting the generically or specifically described reactants and/or operating conditions of this invention for those used in the preceding example.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. In a process for the separation of $C_{5+}$ hydrocarbons from a gaseous feedstream containing light hydrocarbons and optionally components more volatile than methane wherein the gaseous feedstream under pressure is cooled, partially condensed, and separated into a liquid fraction, the latter being subjected to pressure reduction and then separated by rectification in a rectification column into a product stream consisting essentially of $C_{5+}$ hydrocarbons and into a residual gas stream containing predominantly lower-boiling components, the improvement comprising introducing the gaseous fraction separated after the partial condensation without substantial reduction in pressure into a recontacting column wherein said gaseous fraction is scrubbed with a scrubbing liquid to remove residual $C_{5+}$ hydrocarbons from said gaseous fraction, said scrubbing liquid being obtained by partial condensation of said residual gas from the rectification; withdrawing resultant loaded scrubbing agent from the recontacting column; pressure reducing said loaded scrubbing agent; and passing same into the rectification column.

2. A process according to claim 1, wherein said loaded scrubbing liquid introduced into the column is employed as reflux liquid therein.

3. A process according to claim 1, wherein the rectification is conducted under conditions so as to yield a minor portion of $C_3$ and $C_4$ hydrocarbons in the liquid product stream containing $C_{5+}$ hydrocarbons, and to yield the residual gas overhead stream free of $C_{5+}$ hydrocarbons.

4. A process according to claim 1, wherein the residual gas from the rectification is liquefied to an extent of 50–99%, prior to its introduction into the recontacting column.

5. A process according to claim 1, wherein the residual gas from the rectification is liquefied to an extent of 70–95%, prior to its introduction into the recontacting column.

6. A process according to claim 1, wherein the liquid fraction, prior to rectification, is heated at least partially against the gaseous feedstream to be cooled.

7. In an apparatus for conducting the process of claim 1, comprising at least one heat exchanger for the cooling and partial condensation of a gaseous stream, a phase separator having a liquid space and a vapor space for separating partially condensed portion of the gaseous stream, a rectifying column having a head and bottom for separation of the partially condensed portion of the gaseous stream, the improvement comprising a recontacting column, the lower zone of which is in communication with the head of the rectifying column, a heat exchanger, a further phase separator, and a pump positioned between the head of the rectifying column and the upper zone of the recontacting column.

8. A process according to claim 1, wherein after the partial condensation of the residual gas from the rectification, resultant liquid is separated from uncondensed residual gas, and the thus-obtained liquid fraction is pumped to a higher pressure before being introduced into the recontacting column.

9. A process according to claim 8, further comprising discharging said uncondensed residual gas from the rectification under low pressure as a residual gas stream.

10. A process according to claim 1, further comprising withdrawing scrubbed gaseous fraction from the recontacting column, subjecting same to further cooling and partial condensation to provide an additional liquid fraction and an additional gaseous fraction, and separating the thus-obtained additional liquid fraction by a further rectification into an additional product stream consisting essentially of $C_{2+}$ or $C_{3+}$ hydrocarbons and into an additional residual gas stream containing predominantly lower-boiling components.

11. A process according to claim 10, further comprising at least partially engine-expanding the additional residual gas stream and conducting the first mentioned rectification at a pressure between the pressure of the gaseous stream to be separated and the pressure of the engine-expanded, additional residual gas stream.

12. A process according to claim 11, further comprising admixing uncondensed residual gas from the first mentioned rectification to the engine-expanded portion of the additional residual gas.

13. A process according to claim 1, wherein the partial condensation is conducted at between 10° and −15° C.

14. A process according to claim 13, wherein the partial condensation of the residual gas from the rectification is conducted at temperatures of between −25° and −50° C.

15. A process according to claim 14, wherein the residual gas from the rectification is liquefied to an extent of 50–99%, prior to its introduction into the recontacting column.

16. A process according to claim 14, wherein the residual gas from the rectification is liquefied to an extent of 70–95%, prior to its introduction into the recontacting column.

17. A process according to claim 1, wherein the partial condensation of the residual gas from the rectification is conducted at temperatures of between −25° and −50° C.

18. A process according to claim 17, wherein the residual gas from the rectification is liquefied to an extent of 50–99%, prior to its introduction into the recontacting column.

19. A process according to claim 17, wherein the residual gas from the rectification is liquefied to an extent of 70–95%, prior to its introduction into the recontacting column.

20. An apparatus according to claim 19, wherein said phase separator and the recontacting column are arranged in a common housing.

21. Apparatus according to claim 20, wherein the recontacting column is located above the phase separator and a flue plate separating the recontacting column from the phase separator.

22. In a process for the separation of $C_{5+}$ hydrocarbons from a gaseous feed stream containing light hydrocarbons and optionally components more volatile than methane, wherein the gaseous feedstream under pressure is cooled, partially condensed, and separated into a liquid fraction, the latter being subjected to pressure reduction and then separated by rectification in a first rectification column into a product stream consisting essentially of $C_{5+}$ hydrocarbons and a residual gas stream containing predominantly lower-boiling components, the improvement comprising introducing the gaseous fraction separated after the partial condensation into a recontacting column wherein said gaseous fraction is scrubbed with a scrubbing liquid to remove residual $C_{5+}$ hydrocarbons from said gaseous fraction, said scrubbing liquid being obtained by partial condensation of said residual gas from said first rectification column; withdrawing resultant loaded scrubbing agent from the recontacting column; pressure reducing said loaded scrubbing agent and passing same into said first rectification column; withdrawing scrubbed gaseous fraction from the recontacting column and subjecting same to further cooling and partial condensation to provide an additional liquid fraction and an additional gaseous fraction; and separating the thus-obtained additional liquid fraction by further rectification in a second rectification column to provide an additional product stream consisting essentially of $C_{2+}$ or $C_{3+}$ hydrocarbons and an additional residual gas stream containing predominantly lower-boiling components.

* * * * *